(12) United States Patent
Winterberg et al.

(10) Patent No.: US 9,482,526 B2
(45) Date of Patent: Nov. 1, 2016

(54) METHOD FOR REPRESENTING THE SURFACE OF AN OBJECT

(75) Inventors: Horst Winterberg, Bad Feilnbach (DE); Matthias Prams, Rohrdorf (DE); Marcus Steinbichler, Neubeuern (DE)

(73) Assignee: STEINBICHLER OPTOTECHNIK GMBH, Neubeuern (DE)

( * ) Notice: Subject to any disclaimer, the term of this patent is extended or adjusted under 35 U.S.C. 154(b) by 755 days.

(21) Appl. No.: 12/839,632

(22) Filed: Jul. 20, 2010

(65) Prior Publication Data

US 2011/0015901 A1    Jan. 20, 2011

(30) Foreign Application Priority Data

Jul. 20, 2009    (DE) .................. 10 2009 033 886

(51) Int. Cl.
*G06F 17/50* (2006.01)
*G01B 21/20* (2006.01)
*G01N 21/95* (2006.01)

(52) U.S. Cl.
CPC ........... *G01B 21/20* (2013.01); *G01N 21/9515* (2013.01)

(58) Field of Classification Search
CPC .............................. G06F 17/50; G06F 17/5004
USPC ....................................................... 703/1, 7
See application file for complete search history.

(56) References Cited

U.S. PATENT DOCUMENTS

| | | | | |
|---|---|---|---|---|
| 4,629,319 A * | 12/1986 | Clarke et al. | ............... | 356/237.2 |
| 4,920,385 A * | 4/1990 | Clarke et al. | ............... | 356/237.2 |
| 5,216,599 A * | 6/1993 | Uebe | .................. | A61B 10/0012 |
| | | | | 128/920 |
| 5,801,312 A * | 9/1998 | Lorraine et al. | ................. | 73/602 |
| 6,327,374 B1 * | 12/2001 | Piironen et al. | ............... | 382/108 |
| 8,200,003 B2 * | 6/2012 | Michelsson | ................... | 382/145 |
| 2008/0112610 A1 * | 5/2008 | Israelsen et al. | ............. | 382/154 |
| 2011/0320023 A1 * | 12/2011 | Sullivan et al. | ................. | 700/98 |

OTHER PUBLICATIONS

L. Song, NPL, "Three-Dimensional Measurement and Defect Detection Based on Single Image", Apr. 2005.*
Domingo Mery, NPL, "Automated Flaw Detection in Aluminum Castings Based on the Tracking of Potential Defects in a Radioscopic Image Sequence", Dec. 2002.*

* cited by examiner

*Primary Examiner* — Saif Alhija
(74) *Attorney, Agent, or Firm* — Dilworth & Barrese, LLP.

(57) ABSTRACT

In an improved method for the representation of the surface of an object, the actual 3D data (7) of the surface of the object are determined. The desired 3D data of the surface of the object are modified on the basis of the actual 3D data (7) of the surface of the object. The desired 3D data (5) of the surface of the object and the modified desired 3D data (5) of the surface of the object are used as the 3D representation data (FIG. 2).

20 Claims, 2 Drawing Sheets

METHOD FOR REPRESENTING THE SURFACE OF AN OBJECT

BACKGROUND OF THE INVENTION

The invention relates to a method for representing the surface of an object.

A method is known from EP 553 266 B1 for determining the 3D coordinates of the surface of an object in which the surface of the object is sampled by a scanner. The 3D coordinates are determined by an evaluation system in the scanner reference system. A tracking system is furthermore present which can determine the position and direction of the scanner. The absolute 3D coordinates of the surface of the object can be determined by the evaluation system from the 3D coordinates in the scanner reference system and from the data of the position and direction of the scanner in the absolute reference system. These data can be recorded and/or displayed.

EP 995 108 B1 discloses a method for the automatic recognition of surface defects on body shells of automotive vehicles in which a projection apparatus projects a grid structure onto the body shell. The light reflected from the surface of the body shell is received by an optical measurement apparatus and is supplied to a computer system as a measured signal. Surface defects can be recognized in the computer system which can be marked by a marking apparatus.

Methods for representing the surface of an object are used in component inspection, in particular in the automotive industry, but also in other branches of industry. In this respect, the actual 3D data of the surface of the object can be determined by a 3D measurement system. These actual 3D data, which can be present in the form of a scatter plot, for example, can be displayed, in particular on the screen of a computer or of a PC. The surface of the object represented in this manner can be observed and evaluated by a person.

The esthetic, defect-free finish of the visible surface of a product is a decisive quality feature. It allows conclusions on the quality and rating of the product. A high significance is therefore attached to a high-quality surface by quality management, in particular in the automotive industry, but also in other industries.

A number of surface defects, however, only become visible when the surface is shiny and when the environment is reflected in it. The shininess of a surface is usually produced by a surface coating, for example by varnishing, anodization, chromium plating or similar processes. This process step is, however, at the very end of the value creation chain so that the elimination of defects which are only recognized here is frequently no longer possible at all or can only be achieved with a large effort, which is associated with correspondingly high costs.

It is therefore desirable for reasons of economy to be able to recognize surface defects at the earliest possible point in the value creation chain. Surface defects can, however, only be recognized and evaluated with difficulty on matt surfaces.

For example with a body part of an automotive vehicle, a component with a matt surface is produced in a first process stage which takes place in the pressing plant. In a second process stage, a shell is produced whose surface is likewise still matt. The component is only painted in a third process step, which results in a shiny surface. Surface defects can only now be adequately recognized and evaluated.

It had previously been attempted with the help of a complex quality management already to evaluate in advance in the early process stages the surface defects visible later in the finished product. Various aids are used for this purpose, for example whetstones, shine-producing oils, special light sources and similar. On the one hand, all these processes are time-intensive and they require a very large amount of experience by the user. On the other hand, these processes also still leave a large leeway with respect to the very subjective evaluation of the defects.

A further possibility is to convey sample parts through the complete process chain up to painting in order to be able actually to evaluate the appearance on the finished product. This process, however, takes a long time and is very expensive.

SUMMARY OF THE INVENTION

Starting from this, the object of the invention is to propose an improved method for the representation of the surface of an object.

This object is achieved in accordance with the invention by the features herein. In the method for representing the surface of an object, the actual 3D data of the surface of the object are determined. The desired 3D data of the surface of the object are modified on the basis of the actual 3D data of the surface of the object. The desired 3D data of the surface of the object and the modified desired 3D data of the surface of the object are used as the 3D representation data.

It is advantageous if the desired 3D data of the surface of the object are modified in one or more specific regions of the object and are used as 3D representation data. The non-modified desired 3D data of the surface of the object can be used as the 3D representation data in the other regions of the object.

The actual 3D data of the surface of the object can be determined on the basis of a suitable method and/or of a suitable apparatus. Optical 3D measurement devices are suitable, in particular laser measurement devices or white light projection systems. However, measurement instruments working on a tactile basis can also be used. The determination of the actual 3D data of the surface of the object can also be called 3D digitizing or measurement of the object.

The desired 3D data of the object can be stored in an evaluation system, for example in a computer or PC. They can be generated by software and/or by a sampling of a real object or in another manner.

The representation of the surface of the object can take place by an evaluation system, in particular by a computer or a PC. In this respect, the representation takes place on the basis of the 3D representation data. The 3D representation data can be output on the screen of the computer or PC and can be observed and evaluated by a person. They can, however, also be represented and made visible in a different manner.

Advantageous further developments are described herein.

The desired 3D data of the surface of the object can be used as 3D representation data in a specific region of the object or in a plurality of specific regions of the object.

In this respect, it can be a case of one or more predetermined regions which is/are fixed in advance. The predetermined region(s) can be fixed in advance by a person (observer, evaluator). The region(s) can instead or additionally be determined interactively.

The specific region(s) can instead or additionally be determined by an examination of the actual 3D data for surface defects. This examination can be carried out automatically, in particular on the basis of an evaluation algorithm which can be realized by software. The actual 3D data can be used for the determination of the surface defects in the manner such that a virtual whetstone is drawn over the actual 3D data representing the surface of the object. Local surface defects can be discovered in this manner. The local curvatures can be determined and evaluated from the actual 3D data in the region of these local surface defects. Another possibility for determining the surface defects is to measure a so-called good part. The actual 3D data of the surface of this good part determined in this manner are used as reference actual 3D data and are stored as required. The actual 3D data of the subsequently measured objects are compared with the reference actual 3D data. Surface defects can be determined from this comparison.

The desired 3D data can be used as the 3D representation data in the other regions. The total region of the object is then made up of regions in which the desired 3D data are used and represented as 3D representation data and of regions in which the modified desired 3D data are used and represented as 3D representation data.

The desired 3D data can be modified by a refining of the desired 3D data and/or by a change of the normal vectors of the desired 3D data. The desired 3D data modified in this manner can be used as 3D representation data.

It is advantageous when the desired 3D data and/or the actual 3D data and/or the modified desired 3D data are present as CAD data. This can facilitate the processing of the data and/or their representation.

It is possible to use the 3D representation data directly for the representation of the surface of the object. The 3D representation data can, however, also be processed before the representation.

It is advantageous if the representation of the object takes place from a selectable observer point of view. The distance of the observer and/or his angle of view can in particular be selected. It can hereby be achieved that defects on the surface of the object can be recognized and evaluated better.

The representation of the object preferably takes place with a selectable surface characteristic. The material of the surface (paint, anodization, chromium plating, etc.), its color and/or its degree of shine can in particular be selected.

In accordance with a further advantageous further development, the representation of the object takes place with a selectable illumination characteristic. It is advantageous if the number of illumination sources, their kind, their positions, their intensities, their directions and/or their radiation characteristics are selectable.

The representation of the object preferably takes place with a selectable environmental characteristic. In particular the surrounding walls, their colors and/or their degrees of reflection can be selected.

In accordance with a further advantageous development, a defect representation can be superimposed on the representation of the object. The representation of the defect(s) can in particular be elevated. It is possible to determine and represent defect data, with the representation preferably taking place in a superimposed manner.

BRIEF DESCRIPTION OF THE DRAWINGS

An embodiment of the invention will be explained in detail in the following with reference to the enclosed drawing. There are shown in the drawing FIG. 1 a section of a CAD model of an object in a view from above.

DESCRIPTION OF THE PREFERRED EMBODIMENTS

Figure 1:
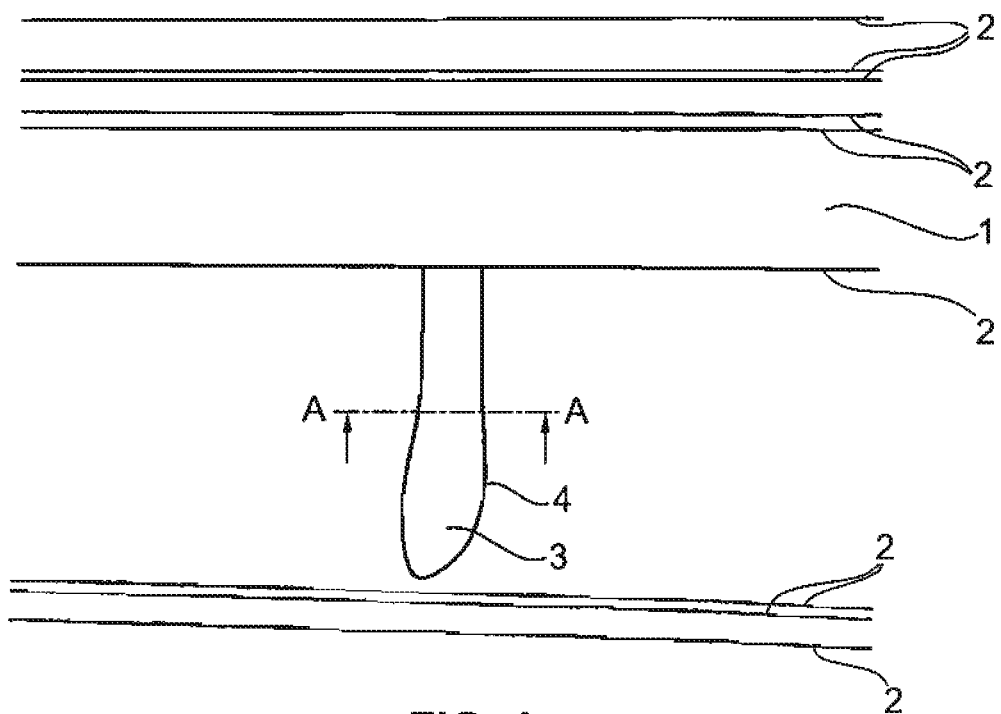

FIG. 1 shows a section of a CAD model of an object 1. The lines 2 are the edges of the construction faces of the CAD model. The CAD model includes the desired 3D data of the object 1.

A surface defect 3 is located at one point of the object 1 and its outline is marked by 4. The outline 4 can be fixed in advance. It is, however, also possible that the outline 4 results from an examination of the actual 3D data for surface defects. This examination can be carried out by a person. It is, however, also possible to carry out the examination on the basis of an evaluation algorithm by software.

Figure 2:
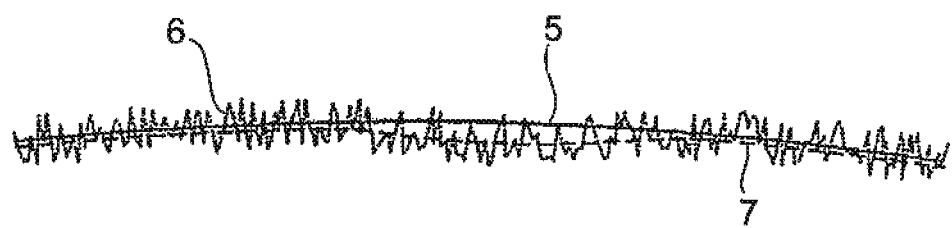
FIG. 2 a section along the line A-A in FIG. 1.

FIG. 2 shows a section along the line A-A in FIG. 1. The curve of the desired 3D data is drawn as solid and is marked by 5. The measured actual 3D data 6, which are drawn as dotted, deviate from this. The actual 3D data 7, which are shown as dashed, are determined by a mean value formation from the originally measured actual 3D data 6. The actual 3D data 7 are smoothed with respect to the originally measured actual 3D data 6.

The desired 3D data 5 are modified on the basis of the actual 3D data 7 in the region of the surface defect 3. The desired 3D data modified in this manner are used as 3D representation data in the region of the surface defect 3. The actual 3D data 7 in the outer regions of FIG. 2 differ only slightly from the desired 3D data 5. The desired 3D data are used as 3D representation data in these ranges. The modified desired 3D data 5 are used as 3D representation data in the middle region of FIG. 2 which lies within the outline 4 of the surface defect 3 (cf. FIG. 1). In the total region of the object 1, either the desired 3D data 5 or the modified desired 3D data are used as 3D representation data and are displayed graphically.

Figure 3:
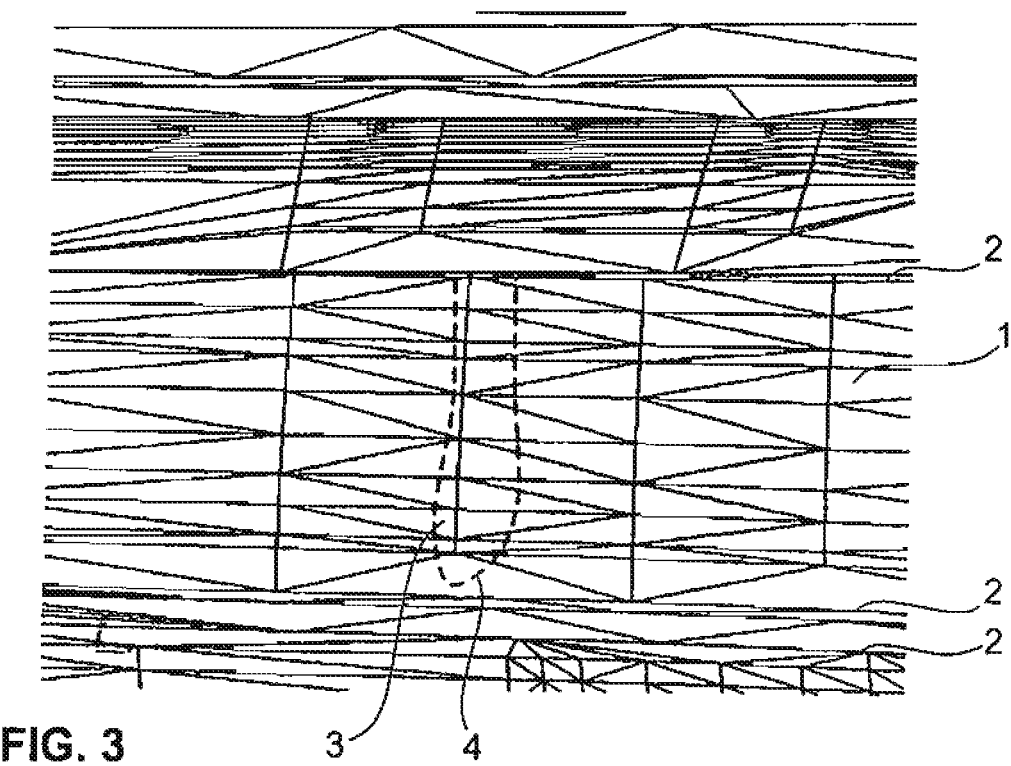
FIG. 3 the CAD model of FIG. 1 as a triangular network.

The desired 3D data 5 and the modified desired 3D data, which are used as 3D representation data, are in each case present as CAD data. This can be seen from FIGS. 3 and 4. FIG. 3 shows the triangular network of the CAD model of the desired 3D data. The conversion of the CAD model into the triangular network can take place with adjustable precision (chord error). The outline 4 of the surface defect 3 is shown as dashed in FIGS. 3 and 4.

Figure 4:
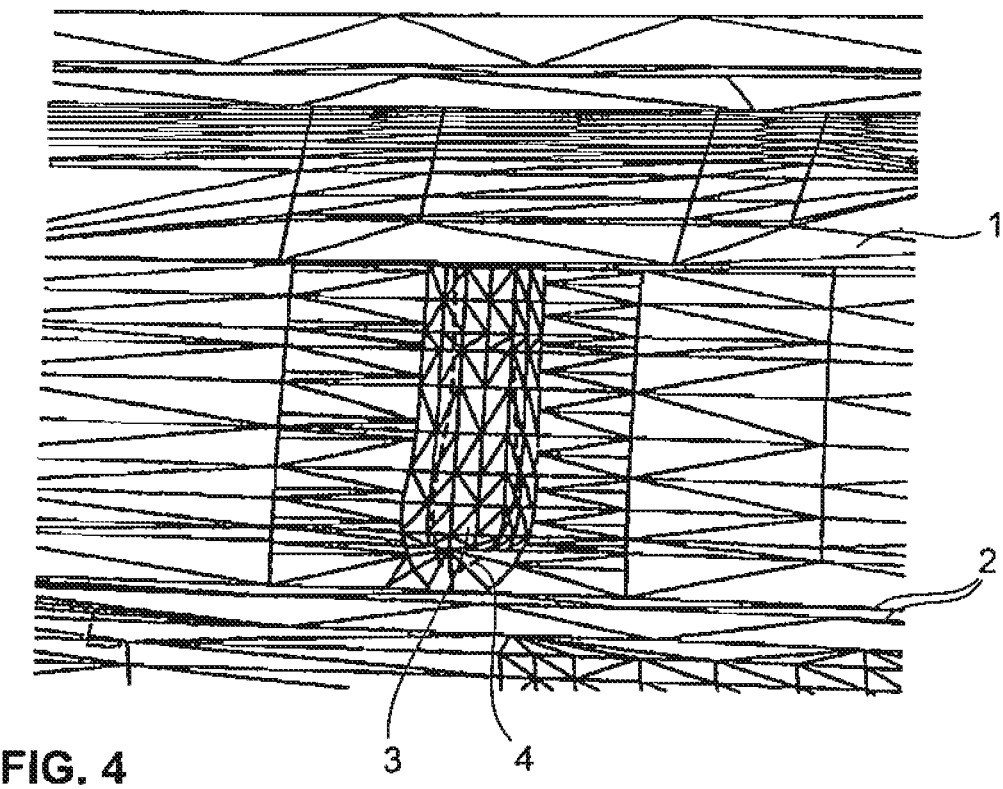
FIG. 4 the triangular network in accordance with FIG. 3 with changes in a specific region.

The desired 3D data are modified on the basis of the actual 3D data and used as 3D representation data in the region of the surface defect 3. The desired 3D data are refined in this region, as can be seen from FIG. 4. Furthermore, in the transition region to the desired 3D data which are used as 3D representation data in the region outside the surface defect 3, the modified desired 3D data which are used as 3D representation data in the region of the surface defect 3 are adapted to these desired 3D data. A transition from the modified desired 3D data to the original desired 3D data which is as smooth as possible should be achieved in this way. The triangular network of the CAD model is changed in a locally limited manner, as shown in FIG. 4, in accordance with the position, extent and 3D contour 4 of the surface defect 3. The change takes place in a manner such that the changed triangular network modulates the 3D curve extent of the surface defect 3 in the region of the surface defect 3.

A system is provided by the invention which enables a simulation of the visual effect of surface defects before the physical surface coating. The later appearance of the real component after the surface coating (painting, anodizing, chromium plating, etc.) can be anticipated by a combination of the measured actual 3D data which include the surface defect contour and of the desired 3D data which originate from the CAD model. In this respect, the measured actual 3D data of the surface are utilized which can be recorded with the help of 3D measurement systems, in particular optical 3D measurement systems. The position and characterization of the surface defects detected on the surface can be utilized.

The surface is visualized on the basis of a 3D computer graphics model with a simulated, coated surface. The position of the observer can be changed as desired, for example in the manner that an observer runs around the surface. The color and degree of shininess of the paint of the surface, the characteristics of the illumination and/or the environment reflected in the surface can be freely selectable by software. The user can in this manner test any desired environmental conditions with respect to the visibility of the surface defects, as if the real object were located in the environment. For example, a showroom at a dealers, an environment in a city, an environment in the country or a quality room with special light ("green room") can be selected as environment. A superimposed representation with defect information is possible. A color-coded relevance, the defect type, the defect size and/or the defect depth and similar can be displayed as the defect information. It is possible to elevate the representation of the defects for better visibility. It is furthermore possible to compare two surfaces directly visually. A comparison can in particular be carried out with a limit sample or a comparison for different production statuses. It is furthermore possible to carry out a direct visual comparison of the actual surface to the CAD model (desired surface).

The invention claimed is:

1. A method for representing a surface of an object (1), comprising the steps of
    measuring actual 3D data (6) using at least one of an optical or tactile 3D measurement device;
    determining actual 3D data (7) of a defect in the surface of the object (1) based on a mean value formation from the measured actual 3D data (6), wherein the actual 3D data and the measured actual 3D data are different sets of data;
    modifying by a computer desired 3D data (5) of the defect of the surface of the object (1) based on the actual 3D data (7) of the surface of the object (1) to generate a modified desired 3D data;
    and generating by the computer 3D representation data that is comprised of the desired 3D data (5) of the surface of the object (1) and the modified desired 3D data of the surface of the object, the 3D representation data displays a 3D image of the surface of the object, wherein the modified desired 3D data depicts a region of the defect in the surface of the object and the desired 3D data depicts an outside region of the region of the defect.

2. The method in accordance with claim 1, wherein the desired 3D data (5) are modified in one or more specific regions of the object (1).

3. The method in accordance with claim 2, wherein the specific region(s) are predetermined and/or determined interactively.

4. The method in accordance with claim 2, wherein the specific region(s) are determined by an examination of the actual 3D data (5) for surface defects.

5. The method in accordance with claim 1, wherein the desired 3D data are modified by a refining of the desired 3D data and/or by a change of normal vectors of the desired 3D data.

6. The method in accordance with claim 1, wherein the desired 3D data (5) and/or the actual 3D data (7) and/or the modified desired 3D data are present as CAD data.

7. The method in accordance with claim 1, wherein the 3D representation data are processed prior to a representation.

8. The method in accordance with claim 1, wherein a representation of the object (1) takes place from a selectable position of an observer.

9. The method in accordance with claim 1, wherein a representation of the object (1) takes place using a selectable surface characteristic, wherein the selectable surface characteristic includes a material of the surface, a color of the surface, or a degree of shine of the surface.

10. The method in accordance with claim 1, wherein a representation of the object (1) takes place using a selectable illumination characteristic.

11. The method in accordance with claim 1, wherein a representation of the object (1) takes place using a selectable environmental characteristic, wherein the environmental characteristics that are selectable include surrounding walls, a color of the walls, and a degree of reflection of the walls.

12. The method in accordance with claim 1, wherein a defect representation is superimposed on a representation of the object (1).

13. The method in accordance with claim 3, wherein the specific region(s) are determined by an examination of the actual 3D data (5) for surface defects.

14. The method in accordance with claim 13, wherein the desired 3D data are modified by a refining of the desired 3D data and/or by a change of normal vectors of the desired 3D data.

15. The method in accordance with claim 4, wherein the desired 3D data are modified by a refining of the desired 3D data and/or by a change of normal vectors of the desired 3D data.

16. The method in accordance with claim 3, wherein the desired 3D data are modified by a refining of the desired 3D data and/or by a change of normal vectors of the desired 3D data.

17. The method of claim 1, wherein the desired 3D data (5) of the surface of the object is data that represents a desired version of the surface of the object, the desired 3D data (5) is a distinct and unrelated set of data from the actual 3D data (7) and the measured actual 3D data (6).

18. The method of claim 9, wherein the material of the surface includes paint, anodization, or chromium plating.

19. The method of claim 1, further comprising:
    visualizing the surface of the object with a simulated coated surface; and
    viewing the surface of the object in a selectable environment,
    wherein a position of a user visualizing the simulated coated surface is changeable.

20. The method of claim 19, wherein the selectable environments include a showroom, a city, a country, or a quality room.

* * * * *